United States Patent [19]

Matejcek et al.

[11] 4,404,226
[45] Sep. 13, 1983

[54] USE OF GUANFACINE IN TREATING SCHIZOPHRENIA

[75] Inventors: Milan Matejcek, Riehen; Carl Theohar, Basel; Horst Kleinlogel, Hinterkappelen, all of Switzerland

[73] Assignee: Sandoz Ltd., Basel, Switzerland

[21] Appl. No.: 395,724

[22] Filed: Jul. 6, 1982

[30] Foreign Application Priority Data

Jul. 9, 1981 [CH] Switzerland .......................... 4512/81

[51] Int. Cl.$^3$ ........................................... A61K 31/155
[52] U.S. Cl. .................................................... 424/326
[58] Field of Search ......................................... 424/326

[56] References Cited

PUBLICATIONS

J. Clin. Pharmac. 7, pp. 221–225 (1967).
Biological Psychiatry 15, pp. 45–57, (1980).
Communications in Psychopharmacology 4, pp. 507–517 (1980).
Chem. Abst. vol. 93, (1980), 125813U.

Primary Examiner—Stanley J. Friedman
Attorney, Agent, or Firm—Gerald D. Sharkin; Robert S. Honor; Joseph J. Borovian

[57] ABSTRACT

This invention provides a new neuroleptic use of a guanidine derivative and novel pharmaceutical compositions for such use.

3 Claims, No Drawings

USE OF GUANFACINE IN TREATING SCHIZOPHRENIA

The present invention relates to a new use for the compound of formula I,

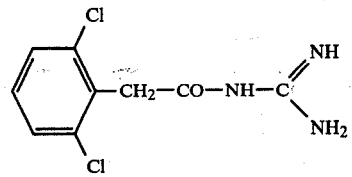

which is the compound N-amidino-2-[2,6-dichlorophenyl]acetamide, also known and referred to throughout the present specification and claims as Guanfacine.

Guanfacine as well as processes for its production are known e.g. from U.S. Pat. No. 3,632,645. The compound is an antihypertensive, commercially available under the name Estulic.

In accordance with the present invention it has now been found that Guanfacine exhibits neuroleptic activity.

The neuroleptic activity is demonstrated in standard experimental clinical studies and clinical trials, e.g. as follows:

In an electroencephalography (EEG) study, unit doses comprising 1 and 2 mg of Guanfacine were administered in one single oral dose at weekly intervals to 10 healthy normotonic subjects using a randomised, double-blind and cross-over design with a placebo as a control. An EEG was recorded before and 1, 2, 4, 6 and 8 hours after administration of Guanfacine. The EEG recordings were evaluated by spectral analysis (see M. Matejcek, "Methodological Considerations in Quantitative Pharmaco-electroencephalography" in "Proceedings of the CINP Congress", Pergamon Press, Oxford 1977, 1151-1164). In this study an increase of delta activities up to 25%, an increase of theta activities up to 10%, and a decrease of alpha and beta activities up to 20% were observed. These changes are indicative of neuroleptic activity (see e.g. T. M. Itil Editor: Psychotropic Drugs and the Human EEG, S. Kaiser, Basel, 1974).

In a 3 centers pilot study clinical trials were conducted in accordance with a rigid protocol regime in which acute paranoid schizophrenics were treated with Guanfacine. The protocol stipulated that the illness had to be of at least moderate (and preferably severe) degree and that the patients were to be in good general health without relevant biochemical abnormality. There was a one week to 10 days wash-out period in the event the patient was being treated with another psychotropic drug.

Guanfacine is administered orally from day 1 till day 42 of the trial to each test-subject individually. The initial dosage of 0.3 mg/day is increased during the trial up to a maximum of 2 mg/day where necessary. The responsiveness of the subject to therapy is determined and monitored using standard rating scales. For example the Fischer Symptom Check List for Neuroleptics records 46 symptoms scored on the basis of their intensity from 0 to 3 (absent, mild, medium, severe) [CIPS-Booklet (Coll. Int. Psych. Scalarum) Beltz, Weinheim, W. Germany, 2nd Edition, 1981]. It is applied on the treatment days 0, 7, 14, 28 and 42. The Brief Psychiatric Rating Scale of Overall and Gorham (Overall and Gorham, Ed. Guy W., ECDEU assessment manual for psychopharmacology, Rev. Ed. Rockville, Md. 1976, 157-169) listing 18 behavioural syndromes which are rated on a score of 1 to 7 ("not present" to "extremely severe") is performed on treatment days 0 and 42. Evaluation of the global therapeutic effect (drug effect, tolerability, fitness for discharge, working or occupational capacity and the overall benefit to the patient) is performed using the Global Impression Scale at the end of the trial. Global assessment scores ranged from 0 to 3 (0=none/bad, 1=fair, 2=good, 3=very good). Blood pressure, pulse rate, laboratory tests of blood, ECG, liver- and kidney-functions are regularly monitored.

Of the 16 patients evaluated, the global assessment of efficacy by the investigating physician who conducted the trial rated the efficacy of Guanfacine as: very good in 1 case, good in 4 cases and fair in 5 cases. There was not significant amelioration in the other 6 cases. The tolerability was excellent in all cases, there were no side effects attributable to the test drug and there was good patient acceptance of the drug.

Guanfacine is therefore useful as a neuroleptic. Accordingly the present invention provides a method of treating schizophrenia which comprises administering to a subject in need of such treatment a therapeutically effective amount of Guanfacine of formula I, in free base form or in pharmaceutically acceptable acid addition salt form.

For the above mentioned novel use the dosage will, of course, vary depending on the mode of administration and therapeutic need. However, in general, satisfactory results are obtained with a daily dosage of from about 0.3 to about 50 mg, preferably from about 0.3 to about 10 mg, e.g. 1 to 2 mg, of Guanfacine. The compound may be conveniently administered in unit dosage form, 1 to 4 times per day. Suitable unit dosage forms contain from about 0.1 to about 50 mg, e.g. about 0.25 to about 5 mg, such as from about 0.25 to about 0.5 mg Guanfacine admixed with a solid or liquid pharmaceutical carrier or diluent.

Guanfacine may be administered in free base form or in pharmaceutically acceptable acid station salt form. Such acid addition salt forms are also known. Preferably the hydrochloride is used.

The activity of such pharmaceutically acceptable salt forms will generally be of the same order as that of the free base form. As used herein all amounts of such compounds recited refer to the corresponding amount of the free base form unless otherwise indicated.

The present invention also provides pharmaceutical compositions for use in the treatment of schizophrenia containing Guanfacine as active agent. These may be prepared in accordance with standard techniques for example by admixture of the active ingredient with conventional compatible pharmaceutically acceptable diluents or carriers, e.g. to prepare solid preparations such as capsules or injectable solutions or suspensions suitable for i.v. administration. Capsule formulations may contain Guanfacine on its own or together with an inert solid diluent, for example, lactose, starch, colloidal silicon dioxide and microcrystalline cellulose. Solutions or suspensions may include e.g. suspending agents such as methylcellulose, tragacanth and sodium alginate, wetting agents such as lecithin, polyoxyethylene stearate and polyoxyethylene sorbitan monooleate and preservatives such as ethyl-p-hydroxy-benzoate. They will generally be presented in sterile ampoule forms suitable for injection. Such forms also include, e.g. known disposable syringe forms. The present invention also provides a pack containing a pharmaceutical composition containing Guanfacine together with instructions for use in the treatment of schizophrenia. The pharmaceutical composition may be in unit dosage form, e.g. tablets or capsules and a number of such unit dosage forms incorporated into a package, e.g. a blister package.

The following examples illustrate compositions suitable for use in the method of the invention: Compositions containing different amounts of Guanfacine may be formulated in analogous manner. Avicel as used hereinafter is a form of microcrystalline cellulose. Aerosil as used hereinafter is a form of colloidal silica. Suppliers of these forms and their properties may be found in H. P. Fiedler, Lexikon der Hilfsstoffe für Pharmazie, Kosmetik und angrenzende Gebiete, 2nd Edition Editio Cantor, Aulendorf, W. Germany.

EXAMPLE 1

Capsule suitable for oral administration

Capsules containing the ingredients indicated below may be prepared by conventional techniques and are administered at a dose of one capsule two to four times a day.

| Ingredient | Weight (mg) |
| --- | --- |
| Guanfacine hydrochloride | 0.288 (~0.25 mg base) |
| Lactose | 144.262 |
| Avicel ® PH 101 | 19.6 |
| Aerosil ® 200 | 0.85 |
| Stearic acid | 5.0 |
| | 170.00 |

Another capsule formulation is as follows:

| | Capsule |
| --- | --- |
| Ingredient | Weight (mg) |
| Guanfacine hydrochloride | 1.15 |
| | (~1 mg base) |
| Lactose | 143.4 |
| Avicel ® PH 101 | 19.6 |
| Aerosil ® 200 | 0.85 |
| Stearic acid | 5.0 |
| | 170.00 |

EXAMPLE 2

Sterile solution for injection

A solution for injection containing the ingredients indicated below may be prepared by conventional techniques, sterilised and filled into pre-sterilised ampoules of 2 ml capacity suitable for injection.

| Ingredient | Weight/Volume |
| --- | --- |
| Guanfacine hydrochloride | 0.6028 mg/ml (~0.5 mg base) |
| Sodium chloride | 9.000 mg/ml |
| 0.1 N Hydrochloric acid at pH 3.7 | q.s. |
| Distilled water | to 1 ml |

EXAMPLE 3

Tablet suitable for oral administration

A tablet containing the ingredients indicated below may be prepared by conventional techniques and is administered at a dose of one tablet two to four times a day.

| Ingredient | Weight (mg) |
| --- | --- |
| Guanfacine hydrochloride | 1.15 (~1 mg base) |
| Lactose | 63.00 |
| Avicel ® PH 101 | 38.85 |
| Polyvinylpyrrolidon | 4.5 |
| Stearic acid | 2.5 |
| | 110.00 |

We claim:

1. A method of treating schizophrenia which comprises administering to a subject in need of such treatment a therapeutically effective amount of Guanfacine of formula I:

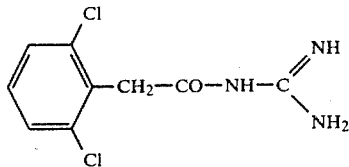

in free base form or in pharmaceutically acceptable acid addition salt form.

2. A method according to claim 1 wherein Guanfacine is administered at a daily dosage of from about 0.3 to about 10 mg.

3. A method according to claim 1 wherein Guanfacine is administered in unit dosage form containing from about 0.25 to about 0.5 mg of Guanfacine.

* * * * *